(12) United States Patent
Dalgard et al.

(10) Patent No.: US 9,782,394 B2
(45) Date of Patent: Oct. 10, 2017

(54) INHIBITORS FOR ERG ONCOGENE POSITIVE CANCERS

(71) Applicant: The Henry M. Jackson Foundation for the Advancement of Military Medicine, Inc., Bethesda, MD (US)

(72) Inventors: Clifton Dalgard, Chevy Chase, MD (US); Ahmed Mohamed, Germantown, MD (US); Meera Srivastava, Potomac, MD (US); Shiv Srivastava, Potomac, MD (US)

(73) Assignee: The Henry M. Jackson Foundation for the Advancement of Military Medicine, Inc., Bethesda, MD (US)

( * ) Notice: Subject to any disclaimer, the term of this patent is extended or adjusted under 35 U.S.C. 154(b) by 0 days.

(21) Appl. No.: 15/125,438

(22) PCT Filed: Mar. 12, 2015

(86) PCT No.: PCT/US2015/020172
§ 371 (c)(1),
(2) Date: Sep. 12, 2016

(87) PCT Pub. No.: WO2015/138722
PCT Pub. Date: Sep. 17, 2015

(65) Prior Publication Data
US 2017/0071920 A1    Mar. 16, 2017

Related U.S. Application Data

(60) Provisional application No. 61/951,743, filed on Mar. 12, 2014.

(51) Int. Cl.
| | | |
|---|---|---|
| *A61K 31/44* | (2006.01) | |
| *A61K 31/4402* | (2006.01) | |
| *C09B 29/28* | (2006.01) | |
| *C09B 67/46* | (2006.01) | |
| *A61K 31/135* | (2006.01) | |
| *A61K 31/136* | (2006.01) | |
| *A61K 31/426* | (2006.01) | |
| *A61K 45/06* | (2006.01) | |

(52) U.S. Cl.
CPC ........ *A61K 31/4402* (2013.01); *A61K 31/135* (2013.01); *A61K 31/136* (2013.01); *A61K 31/426* (2013.01); *A61K 45/06* (2013.01); *C09B 29/28* (2013.01); *C09B 67/009* (2013.01)

(58) Field of Classification Search
CPC .................................................. A61K 31/4402
USPC ........................................................ 514/352
See application file for complete search history.

(56) References Cited

U.S. PATENT DOCUMENTS

| | | |
|---|---|---|
| 5,646,153 A | 7/1997 | Spada et al. |
| 2010/0144832 A1 | 6/2010 | Srivastava et al. |
| 2010/0215638 A1 | 8/2010 | Iljin et al. |
| 2013/0078186 A1 | 3/2013 | Wanker et al. |

OTHER PUBLICATIONS

Fayyaz et al. Immunogenetics (2013) 65:315-332.*
Park et al. Neoplasia vol. 12, No. 7, 2010.*
Shah et al. Human Pathology (2013) 44, 786-794.*
Tsourlakis et al. BMC Cancer (2016) 16:641.*
Paula Amann, Center for Prostate Disease Research, Jun. 23, 2016.*
International Search Report and Written Opinion issued in the corresponding International Application No. PCT/US2015/020172 dated Jun. 16, 2015.

* cited by examiner

*Primary Examiner* — Nizal Chandrakumar
(74) *Attorney, Agent, or Firm* — Morgan, Lewis & Bockius LLP (57) ABSTRACT

Alterations to the ERG gene are some of the most prominent genomic changes associated with many cancers including prostate cancer. Such cancer specific alterations result in the overexpression of wild type ERG protein or an altered ERG protein. The present invention provides selective inhibitors of wild type or an altered ERG protein expression. The ERG inhibitors of the invention, therefore, are therapeutic agents for treating ERG positive cancers.

9 Claims, 7 Drawing Sheets

INHIBITORS FOR ERG ONCOGENE POSITIVE CANCERS

GOVERNMENT LICENSE RIGHTS

This invention was made with government support under HU0001-10-2-0002 awarded by Uniformed Services University of the Health Sciences. The government has certain rights in the invention.

BACKGROUND OF THE INVENTION

The present invention relates to small molecule inhibitors of ERG oncoprotein and the use of such compounds as candidate therapeutics for treating ERG positive cancers, including prostate cancer (CaP). CaP is the most frequently diagnosed non-skin malignancy and second leading cause of cancer related deaths among men in the western countries. While early detected CaP due to PSA screening is managed effectively by surgery or radiation, a significant subset of CaP patients (20% to 40%) experience disease recurrence after definitive treatment and will require hormone ablation therapy. Despite initial response to therapy, metastatic CaP tumors eventually become refractory to hormone ablation therapy. For this subset of patients, namely, those having metastatic hormone refractory cancer there is no effective cure.

The ERG proto-oncogene belongs to a large family of ETS transcription factors that are both positive and negative regulators of gene expression (Watson et al., 2010). These transcription factors are downstream effectors of the mitogenic signal transduction pathways involved in cell proliferation, cell differentiation, development, transformation, apoptosis, and immune regulation (Watson et al., 2010; Sreenath et al., 2011). The ERG gene is the most prevalent and validated genomic alteration in prostate cancer. Recurrent TMPRSS2-ERG gene fusions are present in nearly half of all CaP patients in western countries. This gene fusion results in male hormone dependent and tumor cell specific expression of a truncated ERG protein (deletion of 32 amino terminal residues). ERG alterations and the overexpression of ERG protein, therefore, are implicated in the development and progression of CaP.

ERG expression in CaP is AR dependent. While there are a number of androgen receptor (AR) signaling inhibitors already being used as therapeutics for treating CaP, the present inventors were not previously aware of compounds that can selectively inhibit ERG expression. Accordingly, the invention describes small organic molecules that selectively inhibit ERG expression.

SUMMARY OF THE INVENTION

The invention describes selective inhibitors of ERG oncoprotein and the use of such inhibitors as therapeutic agents for the treatment of ERG positive cancers. In one embodiment, the invention provides a method for treating or preventing a cancer in a patient related to overexpression of wild type ERG protein, an altered ERG protein, increased ERG gene transcription, or increased ERG mRNA translation by administering to the patient a therapeutically-effective amount of an inhibitor of ERG expression alone or in combination with other therapies. Pursuant to one embodiment of the inventive method, the inhibitor selectively inhibits ERG mRNA gene transcription or ERG mRNA translation. According to another embodiment of the inventive method, the inhibitor selectively inhibits the overexpression of wild type ERG protein or an altered ERG protein, or growth of ERG positive tumor cells.

ERG inhibitors used according to the method of the invention selectively inhibit ERG protein expression. Exemplary small molecule compounds that inhibit ERG expression are those selected from the group consisting of or their pharmaceutically acceptable salts.

According to one embodiment, optionally in combination with any other embodiment herein described, treatment is effected by administering the small molecule 1-(thiazol-2-yldiazenyl)naphthalene-2-ol illustrated below as an inhibitor of ERG protein overexpression.

The inventive methodology using one or more of the above described inhibitors of ERG protein overexpression can be used for the treatment of cancer, especially, ERG positive cancers selected from the group consisting of prostate cancer, colorectal cancer, Ewing sarcoma, a vascular tumor and leukemia. Pursuant to one embodiment, optionally in combination with any other embodiment herein described, the method of the invention is used for treating a patient diagnosed with prostate cancer.

The invention also provides inhibitors of ERG oncoprotein expression and the use of such compounds for the treatment or prevention of a cancer related to overexpression of ERG oncoprotein. Also provided is the use of an inhibitor of ERG expression in the manufacture of a medicament for the treatment or prevention of a cancer related to overexpression of ERG oncoprotein.

In some embodiments, optionally in combination with any other embodiment herein described, the invention provides an inhibitor of ERG expression for use in the treatment or prevention of a cancer related to overexpression of wild type ERG protein, an altered ERG protein, increased ERG gene transcription, or increased ERG mRNA translation in a patient suffering therefrom. Processes in which ERG gene transcription and/or translation may increase in subjects include but are not limited to gene fusions, mutations, duplications or other mechanisms. In one embodiment, the inhibitor of ERG expression inhibits the growth of ERG positive tumor cells.

In other embodiments, optionally in combination with any other embodiment described herein, the invention provides a use of an inhibitor of ERG expression for the treatment or prevention of a cancer related to overexpression of wild type ERG protein, an altered ERG protein, increased ERG gene transcription, or increased ERG mRNA translation in a patient suffering therefrom.

Still in other embodiments, optionally in combination with any other embodiment herein described, the invention provides a use of an inhibitor of ERG expression in the manufacture of a medicament for the treatment or prevention of a cancer related to overexpression of wild type ERG protein, an altered ERG protein, increased ERG gene transcription, or increased ERG mRNA translation in a patient suffering therefrom. In one embodiment the inhibitor of ERG oncoprotein inhibits the growth of ERG positive tumor cells.

BRIEF DESCRIPTION OF THE DRAWINGS

FIG. 5 illustrates (A) the inhibition of ERG expression by analogs of ERGi-USU; and (B) the cell growth inhibitory activity of ERGi-USU analogs.

FIG. 6. (A) is a graph showing inhibition of ERG-positive tumor growth xenograft models. The control animals (top curve) exhibited the largest tumor volumes throughout the study, where as mice receiving the highest dose of EGi-USU (bottom curve) exhibited the smallest volumes. (B) is a picture of xenograft tumors harvested from control animals (0 mg/kg). (C) is a picture of xenograft tumors harvested from animals receiving 100 mg/kg. (D) is a picture of xenograft tumors harvested from animals receiving 150 mg/kg.

DETAILED DESCRIPTION

Definitions

A "pharmaceutically acceptable salt" is a pharmaceutically acceptable, organic or inorganic acid or base salt of a compound of the invention. Representative pharmaceutically acceptable salts include, e.g., alkaline metal salts, alkaline earth salts, ammonium salts, water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts. A pharmaceutically acceptable salt can have more than one charged atom in its structure. In this instance the pharmaceutically acceptable salt can have multiple counterions. Thus, a pharmaceutically acceptable salt can have one or more charged atoms and/or one or more counterions.

The terms "treat", "treating" and "treatment" refer to the amelioration or eradication of a disease or symptoms associated with a disease. In certain embodiments, such terms refer to minimizing the spread or worsening of the disease resulting from the administration of one or more prophylactic or therapeutic agents to a patient with such a disease.

The terms "prevent," "preventing," and "prevention" refer to the prevention of the onset, recurrence, or spread of the disease in a patient resulting from the administration of a prophylactic or therapeutic agent.

The term "effective amount" refers to an amount of a compound of the invention, or other active ingredient sufficient to provide a therapeutic or prophylactic benefit in the treatment or prevention of a disease or to delay or minimize symptoms associated with a disease. Further, a therapeutically effective amount with respect to a compound of the invention means that amount of therapeutic agent alone, or in combination with other therapies, that provides a therapeutic benefit in the treatment or prevention of a disease. Used in connection with a compound of the invention, the term can encompass an amount that improves overall therapy, reduces or avoids symptoms or causes of disease, or enhances the therapeutic efficacy of or synergies with another therapeutic agent.

A "patient" includes an animal, such as a human, cow, horse, sheep, lamb, pig, chicken, turkey, quail, cat, dog, mouse, rat, rabbit or guinea pig. The animal can be a mammal such as a non-primate and a primate (e.g., monkey and human). In one embodiment, a patient is a human, such as a human infant, child, adolescent or adult.

Compounds and Methods

The present invention relates to selective ERG inhibitor compounds and to methodologies for using the compounds for treating or preventing a cancer related to overexpression of ETS Related Gene (ERG), wild type ERG protein or an altered ERG protein in a patient. More specifically, the ERG inhibitors of the invention may not attenuate or inhibit androgen receptor (AR) signaling in a majority of AR positive CaP cell lines tested and thus exhibit fewer toxic side effects when compared to therapeutic agents that inhibit AR signaling as the underlying mechanism for treating prostate cancer. Additionally, ERG inhibitors according to the invention inhibit ERG protein in tumor cell lines that do not express AR.

To identify ERG specific small molecule inhibitors, the present inventors screened a library of small molecule compounds, by contacting a TMPRSS2-ERG fusion positive prostate cancer (VCaP) cell line with a fixed concentration of each compound in the small molecule library. ERG protein expression was monitored using an In-cell Western blot assay (LI-COR Biosciences, Lincoln, Nebr.), using a highly specific ERG monoclonal antibody (CPDR ERG-mAb; 9FY) for detection. See Furusato et al., *Prostate Cancer Prostatic Dis.*, 13:228-372 (2010); Mohamed et al., *J. Cancer*, 1:197-208, (2010); Miettinen et al., *Am. J. Surg Pathol.*, 35:432-41 (2011); and U.S. patent publication No. 2012/0135018A1.

This preliminary screen identified a subset of small molecule inhibitors that were further evaluated by quantitative RT-PCR and western blot analysis for their ability to inhibit the expression of ERG mRNA and protein respectively. Based on consistent inhibition of ERG mRNA and protein expression, two small molecules NSC139021 (ERGi-USU) and NSC99629 were chosen for further biochemical and cell growth inhibition studies.

Figure 1:
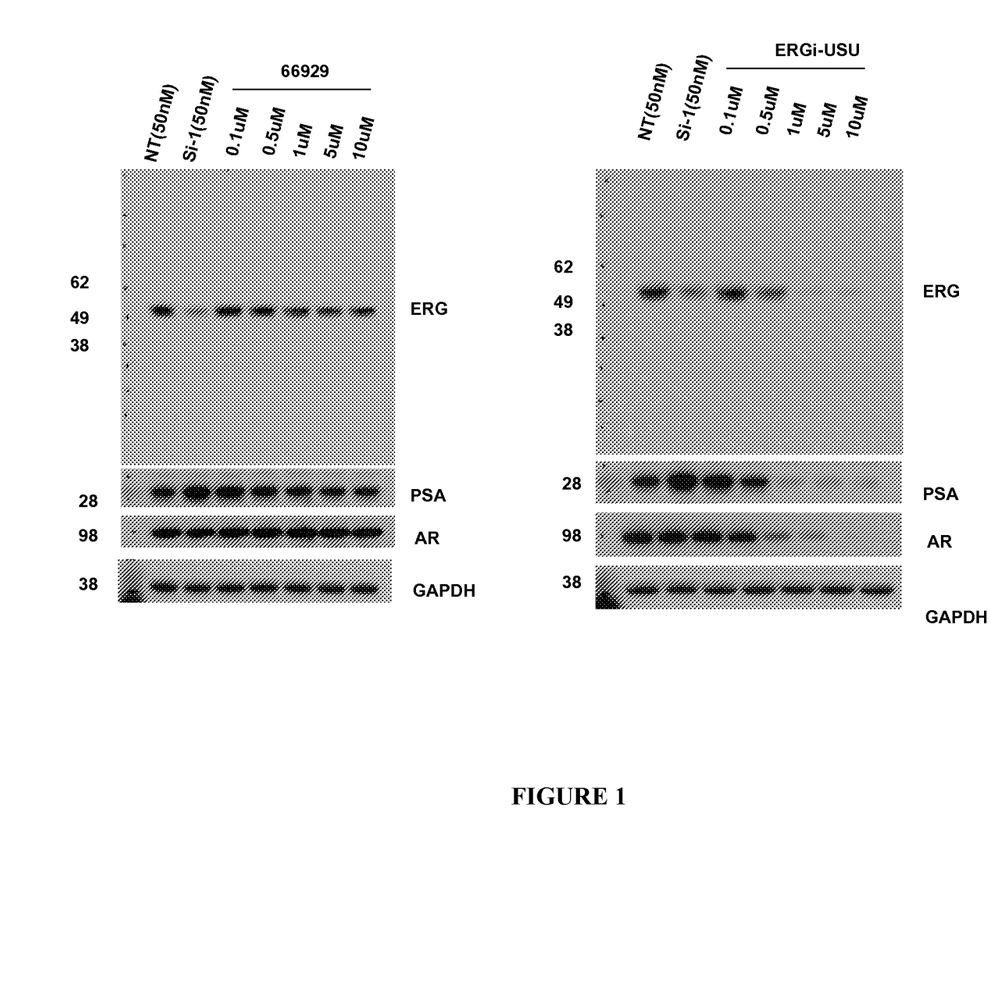
FIG. 1 illustrates the inhibition of ERG, AR, and PSA protein levels by ERGi-USU (139021) and NCS-66929 in VCaP cells.

Approved strategies for treatment of prostate cancer routinely entail therapeutic agents that attenuate or inhibit the activity of AR in prostate cancer cells. Because the expression of ERG in VCaP prostate cancer cells is regulated by AR, the present inventors proceeded to evaluate if the observed ERG inhibitory activity was a result of AR inhibition by ERGi-USU and NSC99629. As illustrated in FIG. 1 and further described below, ERGi-USU but not NSC99629 inhibited the expression of AR and prostate specific antigen (PSA) in VCaP prostate cancer cells.

ERGi-USU

To investigate whether ERGi-USU is a selective inhibitor of ERG protein expression, the compound was further tested for its ability to inhibit AR and PSA activity in the following AR positive/ERG negative prostate cancer cell lines: LNCaP and MDA PCa2b (mutant AR positive and ERG negative), as well as in LAPC4 cells that are AR (wild type) positive and ERG negative.

Figure 2:
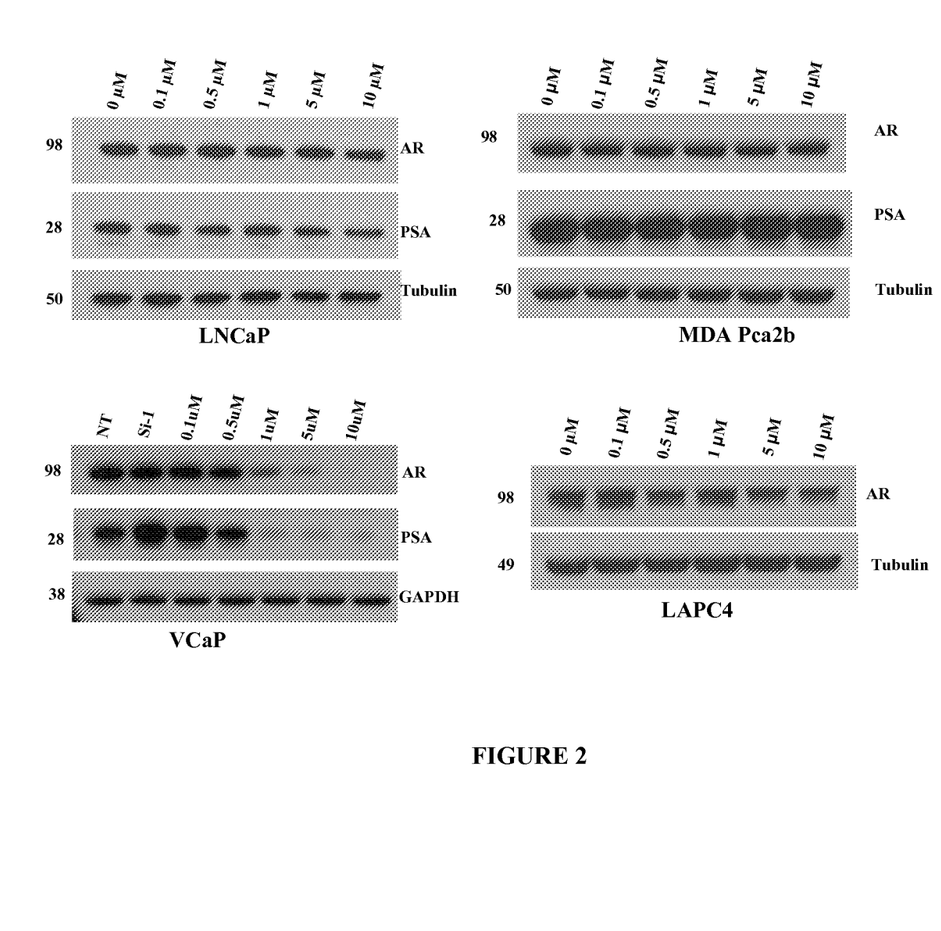
FIG. 2 illustrates the effect of ERGi-USU on AR expression in ERG positive and ERG negative CaP cells.

As illustrated by gel electrophoretic analysis (see FIG. 2), and further described below, inhibition of AR by ERGi-USU is specific to VCaP cells. No AR inhibition was observed in other Ar positive/ERG negative cell lines used in this screen.

In one embodiment the invention provides, therefore, a method for treating or preventing a cancer related to overexpression of wild type ERG protein or an altered ERG protein product of the E-twenty six Related Gene (ERG) in a patient by administering to the patient a therapeutically-effective amount of an inhibitor of ERG expression. The inventive inhibitor selectively inhibits ERG expression. While the exact mechanism by which ERG expression is lowered or inhibited is unknown, the inventive compounds may influence ERG mRNA gene transcription, ERG mRNA translation, prevent ERG protein for attaining its functionally active tertiary structure or inhibit the growth of ERG positive tumors by altering the regulation of a gene that is essential for cell growth.

Figure 3:
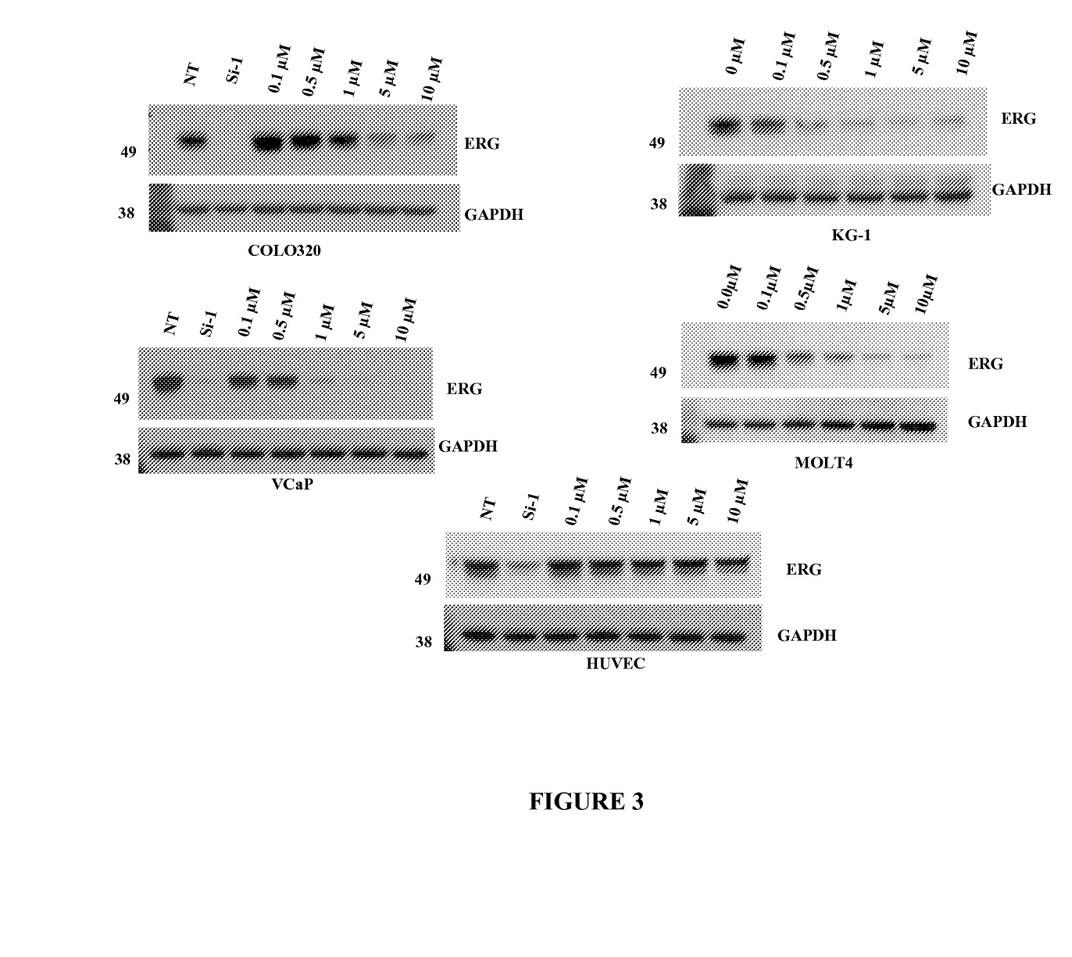
FIG. 3 illustrates the effect of the ERGi-USU on ERG protein expression in ERG positive tumor cell lines and normal endothelial cells.

Studies by the present inventors indicate that ERGi-USU selectively inhibits ERG expression in cancer cells without inhibiting the expression of ERG in normal endothelial cells. As illustrated in FIG. 3, ERGi-USU inhibits expression of ERG in a dose dependent manner in ERG positive cancer cell lines. No measurable inhibition of ERG protein expression was observed in normal HUVEC cells, however.

ERG overexpression in cancer cells is believed to play a role in the development of oncogene addiction, a condition in which some ERG positive cancer cells depend on the activity of the ERG protein for their growth and survival Inhibition or attenuation of ERG protein expression in ERG positive cancer cells, therefore, may arrest the growth and survival of cancer cells. As illustrated by the results of a cell growth inhibition study (see FIG. 4), inhibition of ERG expression prevents growth of ERG positive cancer cells. No cell growth inhibition effects were observed, however, for ERG negative prostate cancer cell lines, an ERG negative immortalized benign prostate cell line (BPH1), and for ERG positive normal cells. These results support the use of ERGi-USU as a candidate therapeutic agent for the selective treatment of ERG positive cancers, such as prostate cancer. Methods for treating ERG positive cancers using the small molecule ERGi-USU, therefore, provides a novel approach for treating metastatic hormone refractory prostate cancer that is unresponsive to treatment with agents that attenuate or inhibit AR activity and/or ablate hormonal activity. Inhibitors of ERG overexpression according to the invention are also used in combination with one or more other therapeutic agents capable of treating cancers. According to one aspect of this combination therapeutic regimen, the inventive inhibitors of ERG overexpression are used in combination with known inhibitors of AR activity for the treatment of prostate cancer, particularly for patients diagnosed with prostate cancer in which the AR activity is amplified or super activated.

Some embodiments of the invention provide additional compounds, identified as ED-1, ED-2, and ED-3, respectively, that also selectively inhibit the expression of ERG protein in ERG positive cancer cells.

ERGi-USU

Each compound was further evaluated as a candidate therapeutic agent for treating a patient having an ERG positive cancer. Separate cultures of ERG positive VCaP prostate cancer cells and ERG negative LNCaP cells were used to test for selective inhibition of ERG expression and the cell growth inhibitory activity of each compound. As further described below and illustrated by FIGS. 5A and 5B, ED-1, ED-2 and ED-3 are selective inhibitors of ERG expression and growth of ERG positive cancer cells.

The above observations and the role of ERG in cancer cell growth supports the use of ERG specific inhibitors as therapeutics for treating cancers such as prostate cancer, colorectal cancer, Ewing sarcoma, a vascular tumor and leukemia. In one embodiment, the subject receiving treatment for cancer according to a method of the invention is a mammal. For instance, the methods and uses described herein are suitable for treatment of cancers in humans. Alternatively, the methods and uses of the invention may be suitable in a veterinary context, wherein the subject includes, but is not limited to, a dog, cat, horse and cow.

In select embodiments of the invention, the ERG inhibitors are co-administered with at least one anti-cancer therapeutic. As used herein, "coadminister" indicates that each of the at least two components is administered during a time frame wherein the respective periods of biological activity or effects overlap. Thus the term coadminister includes sequential as well as coextensive administration of the individual components of the present invention. Accordingly, "administering" the combination of components according to some of the methods of the present invention includes sequential as well as coextensive administration of the individual components of the present invention. Likewise, the phrase "combination of compounds" or "combination of components" and the like indicate that the individual components are coadministered, and these phrases do not necessarily mean that the compounds must be administered contemporaneously or coextensively. In addition, the routes of administration of the individual components need not be the same. In one embodiment, the components of the present invention are administered in the same composition.

In specific embodiments, at least one ERG inhibitors of the present invention can be co-administered with a prostate cancer therapy. In more specific embodiments, the ERG inhibitors are co-administered with one or more of luteinizing hormone-releasing hormone (LHRH) analogs, such as bit not limited to, leuprolide (Lupron®, Eligard®), goserelin (Zoladex®), triptorelin (Trelstar®), degarelix (Firmagon®), Abiraterone (Zytiga®) and histrelin (Vantas®). In other specific embodiments, the ERG inhibitors are co-administered with one or more of anti-androgen receptors, such as bit not limited to, flutamide (Eulexin®), bicalutamide (Casodex®), Enzalutamide (Xtandi®) and nilutamide (Nilandron®). In other specific embodiments, the ERG inhibitors are co-administered with one or more chemotherapeutics such as but not limited to Docetaxel (Taxotere®), Cabazitaxel (Jevtana®), Mitoxantrone (Novantrone®), Estramustine (Emcyt®), Doxorubicin (Adriamycin®), Etoposide (VP-16), Vinblastine (Velban®), Paclitaxel (Taxol®), Carboplatin (Paraplatin®) and Vinorelbine (Navelbine®).

In one embodiment, the ERG inhibitors are administered as a first line therapy. In other embodiments, the ERG inhibitors are administered as a second line therapy or third line therapy. In still other embodiments, the ERG inhibitors are administered later than a third line therapy. As used herein, a first line therapy is the therapeutic regimen that is first prescribed or followed upon diagnosis of a condition that warrants the use of an ERG inhibitor, such as but not limited to prostate cancer. A second line therapy is the therapeutic regimen that is prescribed or followed upon diagnosis of a recurrence or metastasis of condition that warrants the use of an ERG inhibitor, such as but not limited to prostate cancer. Likewise, a third line therapy is the therapeutic regimen that is prescribed or followed upon diagnosis of a second recurrence or metastasis of condition that warrants the use of an ERG inhibitor, such as but not limited to prostate cancer. A therapy, for the purposes of determining which "line" of therapy as used herein, need not be a drug therapy. For example, a first line therapy, as used herein, may be surgical removal, or radiation therapy. Any therapy designed to remove, reduce or ablate the tumor or condition can be considered a "line" of therapy.

In other embodiments, the ERG inhibitors can be administered herein as a "maintenance" therapeutic. As used herein, a maintenance therapeutic is a therapeutic regimen that is prescribed or followed while the subject is free of any detectable condition requiring treatment, for example, after a tumor is surgically removed from the subject. In these embodiments, the ERG inhibitors can be taken, for example, after surgical resection, for a specified period of time, such as but not limited to at least about six months, one year, two years, three years, four years or five years, after the removal or disappearance of the tumor or cancer.

Pharmaceutical Formulations, Routes of Administration and Dosing Regimen

Despite evidence generally associating ERG expression with cancer cell growth, the present inventors were unaware of any compound that selectively inhibits expression of ERG in cancer cells or the use of selective ERG inhibitors as anti-neoplastic agents. The present invention provides compounds and their pharmaceutical compositions that are useful in treating a subject suffering from an ERG positive cancer, as more generally set forth above.

The compound or composition of the invention can be formulated as described hereinabove and is suitable for administration in a therapeutically effective amount to the subject in any number of ways. A therapeutically effective amount of a compound as described herein depends upon the amounts and types of excipients used, the amounts and specific types of active ingredients in a dosage form, and the route by which the compound is to be administered to patients. However, typical dosage forms of the invention comprise a compound or a pharmaceutically acceptable salt of the compound.

Typical dosage levels for the inventive compounds generally range from about 0.001 to about 100 mg per kg of the patient's body weight per day which can be administered in single or multiple doses. An exemplary dosage is about 0.01 to about 25 mg/kg per day or about 0.05 to about 10 mg/kg per day. In other embodiments, the dosage level is from about 0.01 to about 25 mg/kg per day, about 0.05 to about 10 mg/kg per day, or about 0.1 to about 5 mg/kg per day.

A dose can typically range from about 0.1 mg to about 2000 mg per day, given as a single once-a-day dose or, alternatively, as divided doses throughout the day, optionally taken with food. In one embodiment, the daily dose is administered twice daily in equally divided doses. A daily dose range can be from about 5 mg to about 500 mg per day, such as, for example, between about 10 mg and about 300 mg per day. In managing the patient, the therapy can be initiated at a lower dose, perhaps from about 1 mg to about 25 mg, and increased if necessary up to from about 200 mg to about 2000 mg per day as either a single dose or divided doses, depending on the patient's global response.

ERG inhibitor compounds according to the invention may be administered by oral, parenteral (e.g., intramuscular, intraperitoneal, intravenous, ICV, intracisternal injection or infusion, subcutaneous injection or implant), inhalation, nasal, vaginal, rectal, sublingual, or topical (e.g., transdermal, local) routes of administration. The inhibitors can be formulated, alone or together, in suitable dosage unit formulations containing conventional non-toxic pharmaceutically acceptable carriers, adjuvants and vehicles, that are appropriate for each route of administration.

For instance, suitable oral compositions in accordance with the invention include without limitation tablets, troches, lozenges, aqueous or oily suspensions, dispersible powders or granules, emulsion, hard or soft capsules, syrups or elixirs. Inventive compositions suitable for oral use may be prepared according to any method known to the art for the manufacture of pharmaceutical compositions. For instance, liquid formulations of the inventive compounds can contain one or more agents selected from the group consisting of sweetening agents, flavoring agents, coloring agents and preserving agents in order to provide pharmaceutically elegant and palatable preparations of the ERG inhibitor.

For tablet compositions, typical non-toxic pharmaceutically acceptable excipients include without limitation inert diluents, such as calcium carbonate, sodium carbonate, lactose, calcium phosphate or sodium phosphate; granulating and disintegrating agents, for example, corn starch, or alginic acid; binding agents, for example starch, gelatin or lubricating agents, for example magnesium stearate, stearic acid or talc. The tablets may be uncoated or they may be coated by known coating techniques to delay disintegration and absorption in the gastrointestinal tract and thereby to provide a sustained therapeutic action over a desired time period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

For aqueous suspensions the inventive compound is admixed with excipients suitable for maintaining a stable suspension. Examples of such excipients include without limitation are sodium carboxymethylcellulose, methylcellulose, hydropropylmethylcellulose, sodium alginate, polyvinylpyrrolidone, gum tragacanth and gum acacia.

Oral suspensions can also contain dispersing or wetting agents, such as naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl or n-propyl p-hydroxybenzoate, one or more coloring agents, one or more flavoring agents, and one or more sweetening agents, such as sucrose or saccharin.

Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water can provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Syrups and elixirs may be formulated with sweetening agents, for example glycerol, propylene glycol, sorbitol or sucrose. Such formulations may also contain a demulcent, a preservative, and flavoring and coloring agents.

Compositions for parenteral administrations are formulated in a sterile medium suitable for intravenous, intramuscular or intrathecal delivery. A sterile injectable preparation of the inventive compounds may be in the form of a sterile injectable solution or sterile injectable suspension. Nontoxic, parentally acceptable diluents or solvents, for example, 1,3-butanediol can be used to formulate the parenteral compositions. Among the acceptable vehicles and solvents that may be employed are water, Ringer's solution and isotonic sodium chloride solution. In addition, sterile oils also can be employed as a solvent or a suspending medium. For this purpose any bland fixed oil may be employed including synthetic mono- or diglycerides. In addition, fatty acids such as oleic acid can be used in the preparation of injectables.

Depending on the vehicle used and the concentration of the drug in the formulation, the parenteral formulation can contain other adjuvants such as local anesthetics, preservatives and buffering agents.

EXAMPLES

Cell Lines:

Tumor cell lines VCaP, COLO320, KG-1, MOLT4, LNCaP, and MDA Pca2b were obtained from the American Tissue Culture Collection (ATCC; Manassas, Va.). The cells were grown in ATCC-recommended cell culture media under cell growth promoting conditions as recommended by the supplier. Normal cells, such as HUVEC-primary cultures of human umbilical vein endothelial cells and the RWPE1 cell line established from normal adult prostate epithelial cells immortalized with human papilloma virus 18 were also obtained from ATCC. The BPH1 cell line derived from primary epithelial cell cultures immortalized with SV40 large T-antigen, were a gift from Dr. Simon Hayward (Vanderbilt University Medical Center). LAPC4, a metastatic prostate cancer cell line was a gift from Dr. Charles Sawyer (then at UCLA).

Reagents:

ERG monoclonal antibody (CPDR ERG-MAb; 9FY) was developed and characterized at the Center for Prostate Disease Research. Antibodies for the androgen receptor (AR; sc-816), glyceraldehyde phosphate dehydrogenase (GAPDH; sc-25778), and α-Tubulin (sc-5286) were purchased from Santa Cruz Biotechnology (Santa Cruz, Calif.). Antibody for prostate specific antigen (PSA; A0562012) was obtained from DakoCytomation (Carpinteria, Calif.). Antibodies for apoptosis (9915S) and cell cycle regulator (9932) sampler kits were purchased from Cell Signaling (Danvers, Mass.). Sheep anti-mouse IgG-HRP (NXA931) and donkey-anti rabbit IgG-HRP (NXA934V) were obtained from GE Health Care, Buckinghamshire, UK. Small molecule libraries were obtained from the Developmental Therapeutics Program (DTP) of the National Cancer Institute.

General Protocol for Screening Inhibitors of the ERG Oncoprotein Expression:

The TMPRSS2-ERG fusion positive prostate cancer cell line, VCaP (ATCC), was used to identify small molecule inhibitors of ERG expression. VCaP cells were treated with the appropriate dose of the test compounds for 48 hours. The inhibition of ERG expression was evaluated by an In-cell Western blot assay (LI-COR Biosciences, Lincoln, Nebr.) using the ERG specific CPDR ERG-MAb as further described below.

Selection of ERG siRNA as a Positive Control

Small interfering RNA (siRNA) oligo duplexes (5' CGA CAU CCU UCU CUC ACA UAU 3': si-1; and 5' UGA UGU UGA UAA AGC CUU A 3': si-2) against human ERG gene (Gene ID: 2078; Accession: NM 004449), were purchased from Dharmacon (Lafayette, Colo.) and were evaluated as positive controls for use in the ERG expression inhibition screens. Two siRNAs were chosen to primarily rule out off target or non specific effects. Since both siRNAs showed identical results, si-1 was used in the ERG expression inhibitory studies described below. A non-targeting (NT) siRNA duplex was used as negative control (D-001206-13-20; Dharmacon, Lafayette, Colo.). Cells were cultured in their respective growth medium for 48 hours prior to transfection using a 50 nM concentration of the NT siRNA or ERG siRNA. Lipofectamine 2000® (Invitrogen, Carlsbad, Calif.) was used for transfection.

General Protocol for Evaluating the Inhibitory effects of Test Compounds By Western Blot Analysis:

Cultured cells were treated at specific dosages with each of the test ERG inhibitors. Following incubation of the treated cells for indicated time period, cells were lysed using Mammalian Protein Extraction Reagent (M-PER; Pierce, Rockford, Ill.) containing a protease inhibitor cocktail and phosphatase inhibitor cocktails I & III (Sigma, St Louis, Mo.). Cell lysates containing 50 µg of total protein were electrophoresed through 4-12% Bis-Tris Gel (Invitrogen, Carlsbad, Calif.) and the cellular proteins were transferred to PVDF membrane (Invitrogen, Carlsbad, Calif.). Membranes were incubated at 4° C. for 12 hours with primary antibodies for AR, PSA, GAPDH, α-Tubulin, apoptosis markers and cell cycle regulators. Following exposure to primary antibodies, the membranes were washed with buffer (three times, 5 minutes each at room temperature) followed by incubation with relevant secondary antibodies for 1 hour at 24° C. Finally, the membranes were washed with buffer and developed using the ECL Western blot detection reagent (GE Health Care, Buckinghamshire, UK).

General Protocol for Cell Growth and Tumor Growth Inhibition Studies:

The appropriate ERG positive cancer cells, control ERG negative cells or ERG positive normal cells were grown as adherent monolayers or suspensions in tissue culture dishes using the appropriate growth medium as suggested by the vendor. 48 hours following plating of cells, the appropriate test compound is added to each well of the tissue culture dish at a predetermined concentration. The medium was replenished every 24 hours with fresh growth medium containing the same concentration of the same test compound for indicated period of the cell growth inhibition assay. Percent cell growth inhibition was calculated using a hemocytometer for estimating cell density in each of the test wells of the tissue culture dish and trypan blue dye exclusion microscopy and photography to estimate the fraction of viable cells in each test well.

Male athymic nude mice 6-8 weeks old and weighing 27 to 30 g were purchased from Charles River Laboratories. ERG harboring prostate cancer cells (VCaP) were trypsinized and washed twice with ice-cold PBS, and resuspended in ice-cold 50% matrigel in serum-free DMEM medium. A total of $4 \times 10^6$ cells/0.1 ml/mouse were subcutaneously injected into lower right dorsal flank of the mice. Prior to injection, mice were anesthetized with inhalation anesthesia (isoflurane). Tumor growth was monitored weekly after injection. Three weeks later when tumors were palpable mice were randomly separated into 2 experimental groups and one control group of 7 mice in each group. In the treatment groups mice were injected intraperitoneally (I.P) with 100 mg/kg of ERGi-USU or 150 mg/kg of ERGi-USU while the control group were injected with vehicle (1:1 [v/v], DMSO/PEG300) only. Growth in tumor volume was recorded weekly by digital caliper measurements and tumor volumes calculated using the ½ ($L \times W^2$) formula, where L=length of tumor and W=width. Tumor volumes were compared between treated and control groups with repeated measurements and statistical significance of the results between the groups computed using students t-test and p values calculated.

Example 1: Identification of ERG Specific Small Molecule Inhibitors

The TMPRSS2-ERG fusion positive prostate cancer cell line, VCaP was purchased from the ATCC. Cells were grown in medium using conditions prescribed by the vendor. VCaP cells in logarithmic growth were plated in a tissue culture dish at a cell density of 20,000 cells per well. The plated cells recovered overnight before exposing the cells to a single 1 µM dose for each compound present in a small molecule library (Developmental Therapeutics Program, Approved Oncology Drugs Set II, Diversity Set II, Mechanistic Set, and Natural Products Set, National Cancer Institute (NCI)) and selected compounds from the commercial vendor Spectrum Collection for a period of 48 hours.

Inhibition of ERG expression by the test compounds was determined by an In-cell Western assay (LI-COR Biosciences, Lincoln, Nebr.). The ERG specific monoclonal antibody CPDR ERG-MAb was used as the primary antibody. Briefly, the In-cell Western assay was performed by fixing washed cells with paraformaldehyde, followed by permeabilization of the fixed cells and immunolabeling using the primary antibody. The immunolabeled cells were washed and stained using Sapphire700, DRAQ5 and the secondary IRDye 800.

The tissue culture plates were imaged on a Li-Cor Odyssey Infrared Imaging System and infrared signals were measured to provide values for ERG expression and cell number via DNA staining. These values were corrected for parallax by well position on the 96 well plate. The ratio of corrected ERG expression signal values and cell number signal values were used to generate a single value for ERG expression normalized by cell number to detect wells that were >2.5 standard deviations below the average of all normalized values obtained during the primary screen. The screen was performed in duplicate and compounds that decreased normalized ERG expression in both individual screens were identified as positive-hits. This study identified ten lead compounds, including ERGi-USU as inhibitors of ERG protein expression.

Example 2: Confirmation of ERG Expression Inhibitory Activity of Lead Compounds by Quantitative Analysis of ERG Transcripts The ERG inhibitors identified by the primary screen were used in a quantitative RT-PCR assay to evaluate their ability to inhibit ERG mRNA expression. Briefly, VCaP cells were treated at a concentration of 1 µM with each of the ten compounds for 24 hours. Following incubation with the test compounds the cells are lysed and the total RNA isolated. 200 ng of the total RNA was used for analysis of ERG transcripts by qRT-PCR using a pair of ERG primers specific for the coding sequence of tERG for analysis. This screen identified the following three test compounds NSC139021 (ERGi-USU), NSC72292, and NSC99629, as inhibitors of ERG-mRNA expression.

FIG. 1 illustrates the dose dependent inhibition of ERG protein expression in VCaP cells by NSC 139021 (ERGi-USU) and NSC99629. As shown by the two gels in FIG. 1, ERG siRNA (si-1), used as a positive control strongly inhibits expression of ERG protein in comparison to control siRNA (non-target siRNA: NT). The small molecule ERGi-USU also inhibited expression of ERG in VCaP cells in a dose dependent manner (0.1 µM, 0.5 µM, 1 µM, 5 µM and 10 µM), with greater levels of ERG inhibition observed at a dose of 1 µM and higher. ERGi-USU also inhibits expression of PSA, and AR proteins, particularly, at doses greater than 0.5 µM.

No appreciable inhibition of ERG, AR or PSA expression was observed in VCaP cells treated with NSC99629, however. Taken together, the protein inhibition studies demonstrate that ERGi-USU is an inhibitor of the oncoprotein ERG.

Example 3: ERGi-USU is a Selective Inhibitor of ERG Expression

ERG protein inhibition studies using VCaP cells (above) have indicated that ERGi-USU inhibits AR and PSA proteins in addition to ERG in this cancer cell line. Because expression of ERG in VCaP prostate cancer cells is regulated by AR, further studies using AR positive/ERG negative LNCaP, MDA PCa2b and LAPC4 cells were undertaken to confirm that the observed inhibition of ERG expression in VCaP cells was not a result of AR specific inhibition by ERGi-USU.

Briefly, ERG positive VCaP cells and ERG negative LNCaP, MDA PCa2b and LAPC4 cells in logarithmic growth were plated in 10 cm tissue culture dish at a cell density of $2 \times 10^6$ cells per dish. The plated cells were contacted with 0, 0.1, 0.5, 1.0, 5.0, and 10 µM concentrations of ERGi-USU for a period of 48 hours. Cells from each dish were then processed for Western blot analysis and alterations in the expression of ERG protein were monitored.

As illustrated by gel electrophoretic analysis (see FIG. 2), increasing doses of ERGi-USU in the range from 0.1 µM to 10 µM does not inhibit the expression of AR or PSA proteins in the AR positive/ERG negative cell lines mentioned above. However, both AR and PSA expression were inhibited in VCaP cells, with greater inhibition observed at higher concentrations of ERGi-USU. Because ERG expression in VCaP is regulated by AR, the present inventors have hypothesized that the inhibition of AR concurrently with ERG in VCaP cells, most likely is specific to this prostate cancer cell line context.

Studies by the present inventors have also shown that ERGi-USU selectively inhibits ERG expression in cancer cells without inhibiting the expression of ERG in normal endothelial cells. For instance, ERGi-USU was observed to inhibit ERG expression in a dose dependent manner in the following ERG positive cancer cell lines, COLO320 (colon cancer), KG-1 and MOLT4 (leukemia cell lines) and VCaP (prostate cancer). No inhibition of ERG expression was observed, however, in normal endothelial HUVEC cells. See FIG. 3. This result provides further support for the observation that the small molecule ERGi-USU is a selective inhibitor of ERG expression in cancer cells.

Example 4: ERGi-USU Selectively Inhibits Growth of ERG Positive Tumors

The protein inhibition studies described above indicate that ERGi-USU is a selective inhibitor of ERG expression. To investigate whether ERGi-USU selectively arrested the growth of ERG positive cancer cells without arresting the growth of ERG negative cancer cells, a cell growth inhibition study was carried out using the following cancer and normal cell lines: ERG positive cancer cells (VCaP, COLO320, MOLT-4 and KG-1) cancer cells, ERG negative cancer cells (LNCaP, MDA PCa2b and LAPC4) cancer cells, normal prostate RWPE-1 and BPH-1 cells and normal endothelial HUVEC cells. Each cell line was cultured to achieve cells in logarithmic growth and these cells were then plated in 10 cm wells of a tissue culture dishes at a cell density of $2 \times 10^6$ cells per well. The plated cells were contacted with 0, 0.1, 0.5, 1.0, 5.0, and 10 µM concentrations of ERGi-USU for a period of 2, 4, 6 and 8 days. At the end of each time period, cells are recovered from the test plate, washed and the cell density and viability determined using a hemocytometer and trypan blue dye staining method. Cell growth inhibition was expressed as a graph correlating cell number to the concentration of ERGi-USU.

Figure 4:
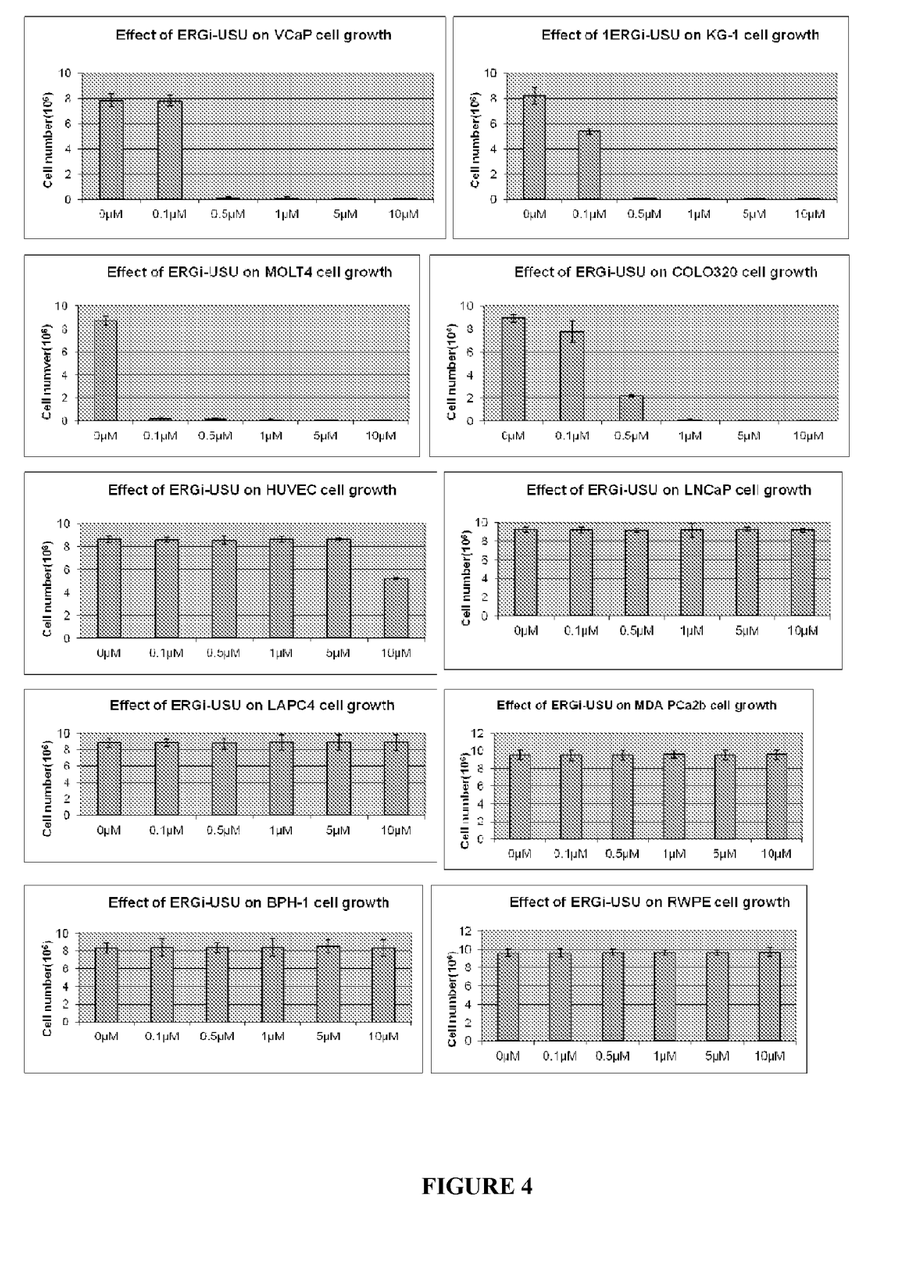
FIG. 4 illustrates the selective inhibition of the growth of ERG positive tumor cell lines versus ERG negative tumor cells or normal cells by the small molecule ERGi-USU.

FIG. 4 illustrates the results of cell growth inhibition studies that were used to calculate the concentration of ERGi-USU needed for inhibiting 50% of the growth ($IC_{50}$) of the cells mentioned above. As illustrated by this figure, ERGi-USU was a potent inhibitor of the growth of ERG positive cancer cells in culture. In contrast, ERGi-USU showed minimal inhibitory effect on the growth of ERG negative cancer cells, normal prostate cells and normal endothelial cells.

Table 1 summarizes the cell growth inhibitory activity of ERGi-USU on ERG positive and ERG negative cells derived from tumor or normal tissue. Based on the $IC_{50}$ values, ERGi-USU inhibits growth of ERG positive cancer cells in the low nanomolar range, for example, $IC_{50}$ values between 50 nM to 300 nM. No cell growth inhibition was observed for ERG negative cancer cells, ERG negative normal cells, as well as for ERG positive normal HUVEC cells, even at inhibitor concentrations greater than 10 µM. Because cell growth arrest was observed only for ERG positive cancer cells, the results in Table 1 demonstrate that ERGi-USU is a therapeutic agent for treating ERG positive cancers, for example, for the treatment of metastatic hormone refractory prostate cancer.

TABLE 1

| Cell line | Tissue origin | ERG/ETV1 gene status | ERG protein inhibition | Cell growth inhibition (ERGi-USU: IC50) |
|---|---|---|---|---|
| VCaP | Metastatic prostate cancer | TMPRSS2-ERG fusion; ERG protein (N-33 aa-del) | Yes | 0.3 µM |
| COLO320 | Colon adenocarcinoma | wt ERG; ERG protein | Yes | 0.3 µM |
| MOLT-4 | Acute lymphoblastic Leukemia | wt ERG; ERG protein | Yes | 0.05 µM |
| KG-1 | Myeloid Leukemia | wt ERG; ERG protein | Yes | 0.2 µM |
| LNCaP | Metastatic Prostate cancer | MIPOL1-ETV1 fusion | N/A | >10 µM |
| MDA PCa2b | Prostate cancer | MIPOL1-ETV1 fusion | N/A | >10 µM |
| LAPC4 | Metastatic Prostate cancer | wt ERG/No ERG protein | N/A | >10 µM |
| RWPE-1 | Normal prostate | wt ERG; No ERG protein | N/A | >10 µM |
| BPH-1 | Normal prostate | wt ERG; No ERG protein | N/A | >10 µM |
| HUVEC | Normal endothelial | wt ERG; ERG protein | No/minimal | >10 µM |

Figure 5A:
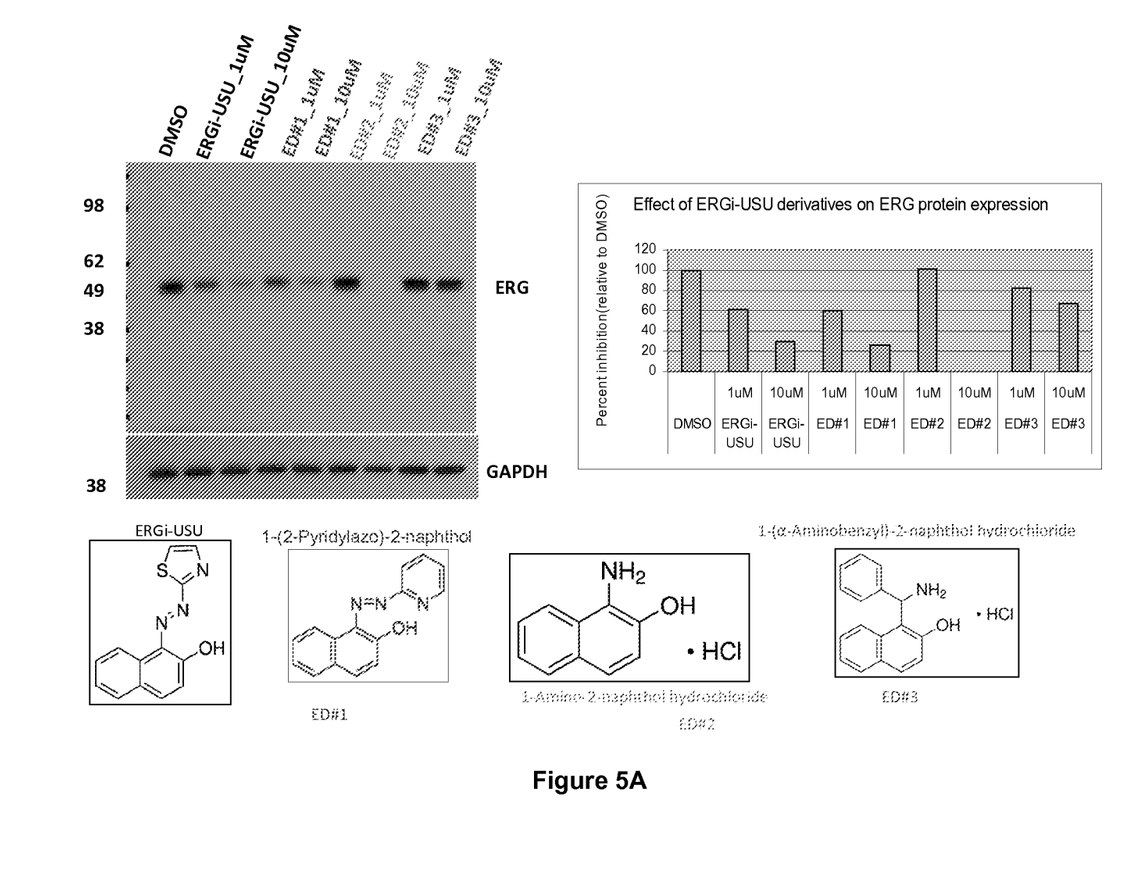
Figure 5B:
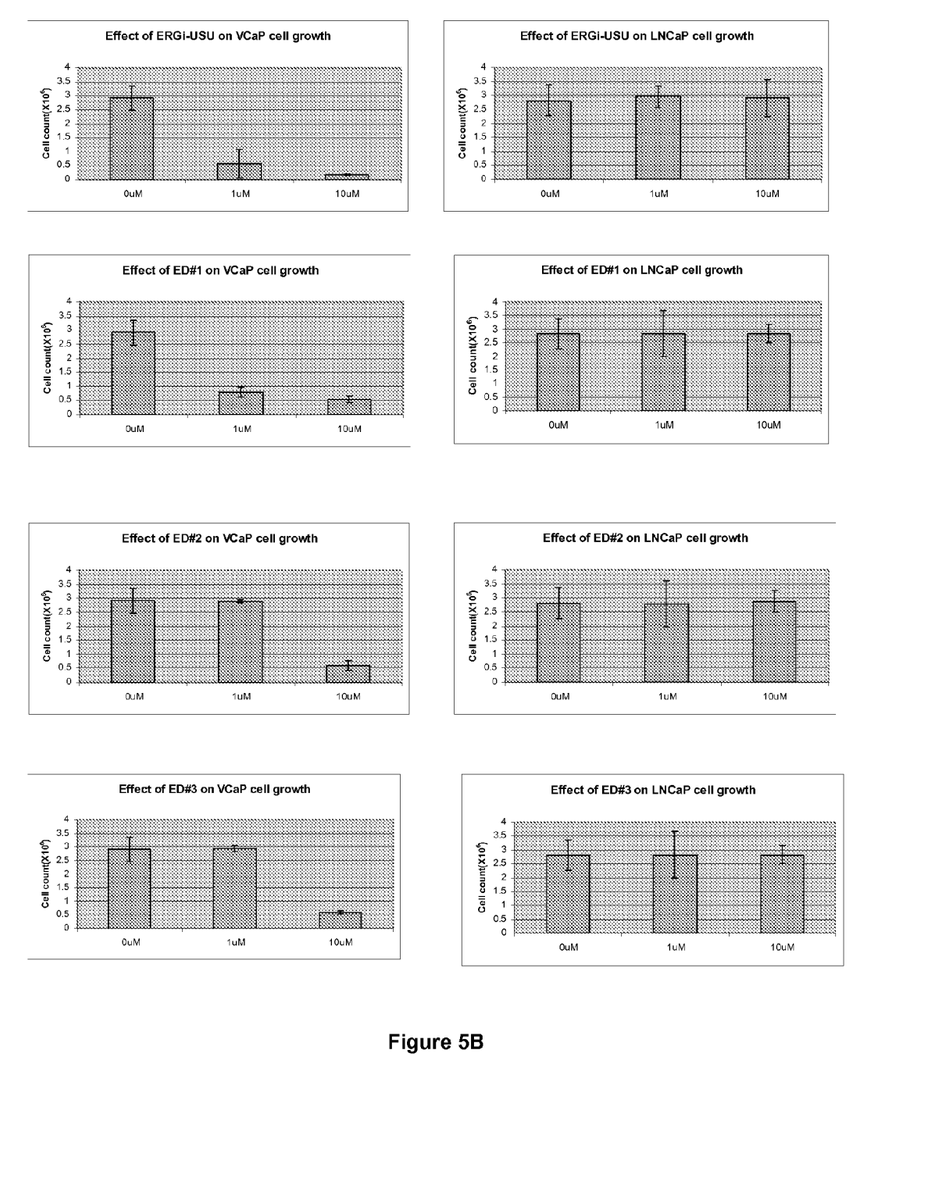

Inhibition of ERG protein expression and cell growth inhibitory activity of three analogs of ERGi-USU, ED-1, ED-2 and ED-3 was also established. ERG protein inhibition by these compounds was evaluated by contacting $2\times10^6$ VCaP cells with 1 µM and 10 µM concentrations of the appropriate inhibitor compound for 24 hours followed lysis of the cells and gel electrophoretic analysis of the cell lysate to quantify the percent inhibition of ERG protein expression. As illustrated in FIG. 5A, each of ED-1, ED-2 and ED-3 inhibits the expression of ERG in VCaP cells. ED-1 and ED-2 are more potent inhibitors of ERG expression than ED-3. FIG. 5A further illustrates that the inhibitory activity of ED-1 and ED-2 were both comparable to ERGi-USU.

ED-1, ED-2 and ED-3 also inhibited the growth of VCaP prostate cancer cells in culture but showed no measurable inhibitory effect on the growth of ERG negative LNCaP cells at doses of 1 µM and 10 µM. See FIG. 5B, where the bar graphs illustrate that ED-1 is a more potent inhibitor of VCaP cancer cells than ED-2 and ED-3. None of the test compounds, however, inhibited growth of ERG negative LNCaP prostate cancer cells in culture. Overall, these results demonstrate that ED-1, ED-2 and ED-3 similar to ERGi-USU, selectively inhibit ERG expression in ERG positive cancer cells and this inhibition of ERG expression, most likely is responsible for the arrest of ERG positive cancer cells in culture. ERGi-USU, its analogs ED-1, ED-2 and ED-3 and their pharmaceutically acceptable salts are useful, therefore, as therapeutic agents for the treatment of ERG positive cancers according to methods of the present invention.

Example 5: ERGi-USU Inhibits Growth of ERG Positive Tumors In Vivo

Figure 6:
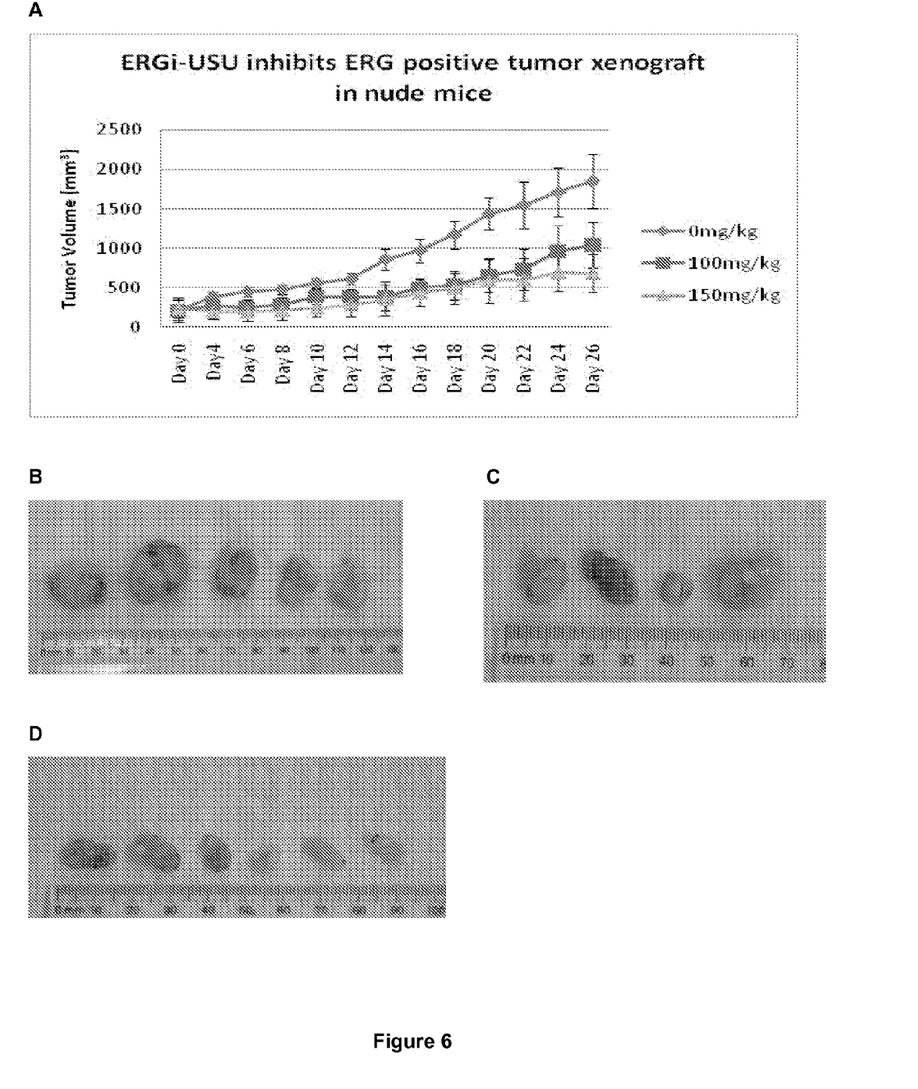

Male nude mice were injected with about $4\times10^6$ VCaP cells and tumor growth was monitored. Tumors began to appear between 4 to 5 weeks post injection, at which time the mice were randomized into two experimental groups and one control group. The treatment groups were injected intraperitoneally with either 150 mg/kg of ERGi-USU or 100 mg/kg ERGi-USU 3 times per week Control animals were also injected 3 times per week with vehicle alone. Tumor growth was monitored weekly. FIG. 6A shows that the control animals (top curve) exhibited the largest tumor volumes virtually throughout the study, where as mice receiving the highest dose of ERGi-USU (bottom curve) exhibited the smallest volumes.

We claim:

1. A method for treating an ERG positive cancer, comprising the step of administering to the patient a therapeutically-effective amount of a compound selected from the group consisting of -continued and wherein the ERG positive cancer is prostate cancer, colorectal cancer, acute lymphoblastic leukemia or myeloid leukemia.

2. The method according to claim 1, wherein the compound selectively inhibits an altered ERG protein.

3. The method according to claim 1, wherein the compound selectively inhibits ERG gene transcription or ERG mRNA translation.

4. The method according to claim 1, wherein the compound inhibits the growth of ERG positive cancer cells.

5. The method according to claim 1, wherein the compound is

6. The method according to claim 1, wherein the ERG positive cancer is prostate cancer.

7. The method according to claim 1, further comprising co-administration of an anti-cancer therapeutic.

8. The method of claim 1, wherein the colorectal cancer is colon adenocarcinoma.

9. The method of claim 5, wherein the wherein the ERG positive cancer is prostate cancer.

* * * * *